United States Patent [19]

de Halleux

[11] Patent Number: 4,569,229

[45] Date of Patent: Feb. 11, 1985

[54] ULTRASONIC PROCESS FOR MEASURING STRESS IN A BOLT OR SIMILAR PART ADAPTED TO THIS METHOD

[76] Inventor: Benoit F. de Halleux, 82, avenue Chevalier Jehan, B-1300 Wavre, Belgium

[21] Appl. No.: 648,163

[22] PCT Filed: Dec. 20, 1983

[86] PCT No.: PCT/BE83/00021

§ 371 Date: Aug. 24, 1984

§ 102(e) Date: Aug. 24, 1984

[87] PCT Pub. No.: WO84/02577

PCT Pub. Date: Jul. 5, 1984

[30] Foreign Application Priority Data

Dec. 24, 1982 [LU] Luxembourg .............. 84553

[51] Int. Cl.⁴ ........................................ G01N 29/00
[52] U.S. Cl. ................................... 73/597; 73/761
[58] Field of Search ..................... 73/597, 379, 761

[56] References Cited

U.S. PATENT DOCUMENTS

| | | | |
|---|---|---|---|
| 3,538,750 | 11/1970 | Lynnworth ............... | 73/597 |
| 3,636,754 | 1/1972 | Lynnworth et al. ...... | 73/597 |
| 3,969,960 | 7/1976 | Pagano .................... | 73/761 |
| 4,014,208 | 3/1977 | Moore et al. ........... | 73/761 |

FOREIGN PATENT DOCUMENTS 1369858 10/1974 United Kingdom .

OTHER PUBLICATIONS

"New Sensors for Ultrasound: Measuring Temperature Profiles", *Materials Research & Standards*, Lynnworth et al., Aug. 1970.
"Panatherm 5010C Ultrasonic Profiler", *Panametrics*, Jun. 1979, pp. 1-4.

*Primary Examiner*—Anthony V. Ciarlante
*Attorney, Agent, or Firm*—Fishman & Dionne

[57] ABSTRACT

The method for measuring strains in a part uses the reflection of an acoustic wave, while measuring a transit time of said wave by means of an apparatus which measures the fade-in time of an echo coming from an interface. The method comprises the steps of selecting within the medium one or a plurality of ends of rectilinear measuring runs, which ends are embodied by an inner artificial reflector (8, 9) emitting of a beam of acoustic waves so that acoustic rays carrying sufficient energy strike the useful reflectors, selecting the echoes corresponding to the reflectors, determining by measurement the transit times which are characteristic of the useful acoustic rays up to the inner artificial reflectors and transposing the transit times for each inner reflector considered individually or the respective differences of transit times for each couple of reflectors into an outer strain value or into a strain value within the region delimited by each couple of reflectors. The part for implementing such method comprises reflectors consisting particularly of perforations or bores into the part.

21 Claims, 8 Drawing Figures

ULTRASONIC PROCESS FOR MEASURING STRESS IN A BOLT OR SIMILAR PART ADAPTED TO THIS METHOD

The present invention relates to a process for measuring stress in a structural element, particularly a high-strength bolt, a threaded rod or a tie, by reflection of acoustic waves.

It also relates to structural elements so adapted as to be able to make the measurement of stress by means of the process according to the invention.

By stress in the sense of the invention should be understood the cause which gives rise to the variation of the transit time of the useful acoustic ray over a path of determined length, which cause may act directly or indirectly.

This may be a variation of the state of internal stress in the usual sense of the term, along the path of the acoustic ray while local temperatures remain constant, or a system of external forces applied to the solid, producing a variation of the state of internal stress, in the usual sense of the term, along the acoustic path.

By prestress of an element we understand a particular technique of utilization of the element, consisting of introducing into the latter an initial tension or compression which will continue to exist, possibly with variable amplitude, whatever the system of loads applied.

The invention is in particular applicable to the measurement of the stress occurring in bolts, threaded rods, and ties, but is not limited to these applications.

The particular feature of high-strength bolts resides in the fact that, when they are fitted, they are subjected to a prestressed state in such a manner as to develop on the surfaces of contact of the elements joined together a local pressure capable of opposing their relative movement through the action of external stresses.

This explains the importance of being able to control and measure the prestress introduced into the body of the bolt when it is tightened.

Since the techniques of mechanical measurement, such as for example the torque wrench, particularly for measuring prestress during tightening, have been found too inaccurate and capable of permitting only with difficulty measurements of residual prestress which are spaced out at intervals of time, other solutions have been sought.

Also, certain authors have proposed measurement of stress by means of acoustic waves.

It is in fact known that the speeds of propagation of acoustic waves, and in particular of longitudinal waves (L waves), transverse waves (T waves), and surface waves (R waves) are dependent on physical parameters of the material medium in which the wave is propagated. As an example, for a homogeneous isotropic medium, the speeds of the L waves, the T waves and the R waves are dependent on the longitudinal modulus of elasticity E, the density $\rho$, and the Poisson's ratio $\mu$. With regard to the Lamb waves, their speed of propagation is in addition dependent on frequency. The speeds of the waves are influenced by all the factors which influence these physical parameters, and in particular by stress and temperature.

The longitudinal and transverse acoustic waves emitted by a plane crystal exhibit, for frequencies dependent on the material medium and the equivalent diameter of the emitting crystal, a property of directivity which permits selective location of anomalies reflecting all or part of the energy of the incident wave, and this is achieved in dependence on the respective positions of the transmitter and also of the receiver and the angle of penetration of the axis of the beam into the material.

In known processes, stress is measured either by measuring the transit time of an ultrasonic wave in the length of the body, for example the bolt, which measurement can be made by an impulse echograph method, or by determination of the resonance frequencies of a sustained wave. The resonance frequencies constitute an arithmetic progression in which the common difference is the fundamental frequency. The inverse of the latter is the minimum transit time of the useful acoustic ray.

Nevertheless, the measurement of stress by ultrasound generally makes use of direct measurement of the transit time of a longitudinal wave or of a transverse wave.

For this purpose a measurement may be made by transmission, by placing an ultrasonic transmitter on one side of the part and a receiver on the opposite side. It is however also possible to make a measurement by reflection by using one or two sensors, which consist of a transmitter and a receiver, most usually combined or separate in one and the same sensor, the measurement then being made by detection of echos resulting from reflections of the wave on the ends of the part and determination of the transit time of the useful acoustic ray by determining the time separating the appearance of the feet of the echo peaks of ends on the representation of type A, each reflection giving rise in fact, if the reflected energy returns to the receiver, to an anomaly echo characterized by a peak in the representation of type A used in usual conventional ultrasonic control apparatus.

The conventional method for determining stress in a bolt consists in suitably disposing a sensor on one end of a bolt and measuring the time required for the useful acoustic ray to travel twice, or a multiple of twice, the length of the bolt, the acoustic ray being partially or completely reflected at the two ends of the bolt.

The transit time in the bolt is dependent on the stress on the run of the useful acoustic ray, because this stress influences the speed of transit and the length of transit.

Nevertheless, the conventional method has numerous disadvantages:

the mechanical component, for example a bolt, does not exhibit uniform stress over the length travelled by the acoustic wave. In the case of the prestressed bolt, the stem is subjected to tension, the head is subjected to a complex force including flexion, the threaded zone is subjected to variable tension, and any free portion of the threaded rod is without stress.

This results in inaccurate knowledge of the length of the tensioned portion of the bolt in which the speed of propagation of the acoustic waves is influenced by the stress, and of the total length of the bolt one part only of which is subjected to stress. A systematic error is therefore committed in the determination of the stress by acoustic waves, except with calibration in an identical configuration. This therefore requires calibration for each position of the nut on the threaded rod and each length of bolt;

in a joint it is rare for the support surfaces of the bolt head and of the nut to be strictly plane and parallel. There is consequently a flexion of the stem of the bolt when it is tightened, and this changes the useful acoustic ray for the measurement and, because of the flexion alone, modifies the length of the characteristic run. Because of the foregoing, this disadvantage introduces a first systematic error into the measurement of stress by acoustic waves. In addition, the local stress introduced by the flexion on the path of the useful acoustic ray modifies the speed of propagation of the useful acoustic ray and consequently falsifies the measurement of the prestressing of the bolt. The lack of parallelism of the ends of the bolt or of the threaded rod, due to flexion, may have the consequence that the reflected acoustic energy does not reach the receiver and makes all measurement impossible when the measurement is made by reflection.

If the two ends of a narrow part, which has plane, parallel surfaces, are not sufficiently perpendicular to the axis, although it is possible to propagate an acoustic wave in the material, if the narrow part is of considerable length it may be difficult, or even impossible, to ensure that a useful acoustic ray will reach the receiver by reflection on one end, so that measurement of stress is impossible.

The exact positioning of the sensor on the end of the bolt is of importance if the reflecting surfaces are not strictly parallel or are not perfectly plane. The information supplied by the acoustic ray of the reflection wave which reaches the receiver and which advantageously has the shortest transit time in the part is in fact utilized. This minimum transit time is then dependent on the position of the sensor on the ends of the part. The width and the opening of the beam are of importance because acoustic rays can be reflected by parasitic reflectors, for example the edges and faces of the screwthreads, before the useful acoustic ray is reflected by the second end of the part. The height of the peaks of the parasitic echos may hamper the selection of the peaks of the useful echoes. In addition, if peaks of parasitic echoes are superposed on peaks of useful echoes, it is no longer possible to determine with great accuracy the minimum transit time of the useful ray, particularly if use is made of a run or a group of runs of the acoustic ray other than the first run. The minimum travel time is in fact ideally determined by the determination of the time separating the feet of the peaks of echoes retained.

The concavity or convexity of the end of the bolt falsifies the measurement of the minimum transit time of the useful acoustic ray for different positions of the sensor on the head, for the same reasons as above.

Attacks by generalized corrosion of the head and end of the bolt give rise to a variation of the reference length, that is to say the run of the ray which has the shortest transit time. In addition, the surfaces of the head and end of the bolt may deteriorate in use, for example through wear, through bruising, through generalized or localized corrosion, in such a manner that the relative position of the sensor in relation to the part has changed. In the usual methods of measuring stress in bolts it is not permissible to grind the ends in order to enable the measurements to be made. Grinding entails in fact a non-quantifiable reduction of the transit length.

Coupling is usually necessary between the sensor or sensors and the part, in order to transmit to the latter a part of the acoustic energy of the transmitter and to receive at the receiver a part of the energy reflected. The thickness of the film of coupling medium between the sensor or sensors and the part influences the measurement of the transit time of the acoustic wave in cases where use is made of the first run of the acoustic waves in the part. The reflection peak of the bottom face of the sensor in fact covers the reflection peak at the entry into the part. The transit time in the coupling medium is then counted as forming part of the transit time in the part. In view of the fact that for the usual dimensions of bolts the variations of the transit time which are utilized for measuring stress are slight, the error made in respect of the transit time of the bolt because of the transit time in the coupling medium may result in a large error in respect of stress. The contact pressure between sensor and part is consequently of importance, because it modifies the thickness of the film of coupling medium.

Some authors propose to eliminate the influences due to the entry of the wave into the material by measuring the time required for the wave to travel a plurality of times over the length of the bolt, the first run being eliminated. This procedure can be applied in practise only with sensors in which the transmitter and receiver are combined, and not with a sensor or sensors having separate transmitters and receivers. It may, however, encounter difficulties due to parasitic echoes originating, among other sources, from any reflections occurring on the faces and the corners of screwthreads. The parasitic peaks due to reflections on screwthreads make the measurement inaccurate, because it may not be possible to determine with the necessary accuracy the minimum transit time of the acoustic ray between the characteristic reflecting surfaces. In these cases, the other disadvantages are not always eliminated.

It has also been proposed in GB-A-1,369,858 to measure an axial force, particularly in a bolt, by using the natural resonance frequency of the object subjected to the measurement, under the action of the different forced oscillations.

The present invention therefore seeks to provide a process for the measurement of stress in a structural element by making use of the reflection of an acoustic ray and by measuring the transit time of the latter with the aid of an ad hoc equipment, for example an equipment determining the time between the feet of two characteristic echo reflection peaks, while eliminating the disadvantages of known processes or at least reducing their impact considerably.

The process of the present invention is comprises one or a plurality of ends of rectilinear measurement paths, having the material form of an internal artificial reflector, being selected in the structural elements, a beam of acoustic waves being transmitted in such a manner that acoustic rays carrying sufficient energy touch the useful reflectors, the echoes corresponding to the reflectors being selected, the transit times characteristic of the useful acoustic rays as far as the internal artificial reflector being determined by measurement, and the transit times for each internal reflector considered individually, or the respective differences of transit time of each pair of reflectors, being transposed into a value of external stress or into a value of stress in the zone delimited by each pair of reflectors.

One preferred practical embodiment of the invention is the embodiment wherein a rectilinear measurement path bounded by two internal artificial reflectors is selected in the medium, wherein a beam of acoustic waves, the axis of which is substantially identical with the selected rectilinear measurement path, is transmitted, wherein the echoes corresponding to the reflectors are selected, wherein the transit time characteristic of an acoustic ray between the two reflectors is measured, this time being the difference between the transit times of the coincident or substantially parallel acoustic rays as far as each of the two reflectors, and wherein the values of transit time are transposed into values of stress.

The characteristic transit time is advantageously the minimum transit time.

For the purpose of the measurement use will advantageously be made of an equipment making it possible to select the feet of peaks due to the internal artificial reflectors, and to obtain the difference between the two transit times of the wave from the transmitter source to the corresponding reflector.

The artificial reflectors are advantageously arranged in such a manner that the run of the acoustic wave is parallel and very close to the neutral line, or even on that line. This arrangement makes it possible for the influences of flexion, which may falsify the measurements in the usual process, to be practically eliminated.

Use is preferably made of a sufficiently narrow ultrasonic beam, which increases the accuracy of the measurement, if it is combined with practically punctiform reflectors or reflectors having a behavior practically similar to that of a punctiform reflector. The beam used will advantageously be focused.

The measurement of the transit time may be made by a continuous transmission and determination of the resonance frequencies of the wave which are due to the internal reflectors. The resonance frequencies constitute an arithmetic progression in which the common difference is the fundamental frequency. The inverse of the latter is the minimum transit time of the useful acoustic ray between the reflectors concerned. The end of the bolt will advantageously be profiled, for example, convexly or concavely in order to eliminate the resonance frequency related to the length of the bolt.

In preference, the measurement of the transit time of the acoustic wave between the two reflectors will advantageously be made with the aid of a thickness measurer making use of ultrasonic waves. The ultrasonic thickness measuring apparatus can in fact be considered as an apparatus which directly or indirectly measures a transit time of an ultrasonic ray in the part.

It is therefore necessary to measure the transit time $t_o$ of the useful acoustic ray between the two artificial internal reflectors when the body is not subjected to a stress.

The transit time t of the acoustic wave between the two internal reflectors when the body is subjected to a stress will then be measured.

The difference between t and $t_o$ is due:

1. to the variation of the speed of the acoustic wave with the stress on the run of the useful acoustic ray,
2. to the variation of the characteristic distance between the internal reflectors because of the stress.

It is necessary to establish a calibration curve linking the stress to the transit time t between the two internal reflectors and making it possible to transpose the transit time values into stress values.

According to an alternative operating procedure, it would be possible to use transverse ultrasonic waves in cases where the stress applied to the body during the calibration stage shows an influence on the characteristic transit time of the useful acoustic ray along the line separating the artificial internal reflectors. However, this gives rise to various difficulties known to those versed in the art, particularly the difficulty of generating this type of wave in the material in the case of propagation normal to the end of the part.

According to an alternative operating procedure, it would be possible to use any type of acoustic wave, particularly ultrasonic surface waves, provided that the stress applied to the body has an influence on the characteristic transit time of the useful acoustic wave as the result of the stress thus created on the line separating the artificial internal reflectors. In this case the artificial internal reflectors would have to be relatively close to the surface, because the surface wave affects only a depth of material of the order of the wavelength.

According to another particularly preferred operating procedure in the case of bolts, threaded rods and ties, use is made of longitudinal ultrasonic waves, which have the advantage, in the case of normal incidence, of being easily transmitted to the part.

It would also be possible to use in combination, and concomitantly or in succession, a longitudinal wave and a transverse wave, which gives an additional datum for determining the stress.

The ratio of the respective transit times of an L wave and a T wave in a sufficiently homogeneous and isotropic medium between two reflectors is equal to the inverse of the ratio of the respective speeds of these two waves, and is solely dependent on the value of the Poisson's ratio $\mu$. It therefore does not depend on the distance between the reflectors. It is thus sufficient to calibrate this ratio of the transit times for the material in dependence on the stress. It is desirable to do this on the component having the reflectors.

In other cases—non-homogeneous or anisotropic media—for example, when the calibrations with each type of wave are applied to the component having the two artificial internal reflectors, it is possible to take into account any other factors influencing the transit time of the wave in the material, such as the temperature for example.

Measurement of stress by ultrasound in the plastic range is possible only if it is possible to be free of the irreversible increase of distances between two reflectors. One way of doing this is to use in combination, and concomitantly or in succession, an L wave and a T wave, provided that the ratio of the two transit times does not depend substantially on plastic deformations, thus making it possible, within sufficiently homogeneous and isotropic media to become independent of the instantaneous distance between the reflectors. This solution could probably be extended to the case of non-homogeneous and/or anisotropic media.

It may also be expected to solve these problems by using two waves, which may or may not be of the same type and which have different frequencies, and to make use of any influence that the frequency may have on the speed of propagation in order to make it possible, in the same way and with the same limitation, to measure stress in the plastic range.

In this case, it would be possible, both for the first solution and for the second, to determine, indirectly with the aid of ad hoc calibration curves made on the material, the amplitude of plastic deformation, working as in the case of a gage which is at one and the same time a stress gage and a plastic deformation gage.

It would also be possible to use in combination, and concomitantly or in succession, two or more acoustic waves of different frequencies in cases where, in a real medium, the speed of an acoustic wave would be sufficiently influenced by the frequency of the wave, whereby one or more additional data for the calibration for determining the stress would be gained.

It would thus be possible to be independent of knowledge of the distance between two internal reflectors, or to take into account other factors influencing the transit time of the wave in the material, such as temperature or, where applicable, plastic deformation, for example.

By selecting a characteristic run subject to uniform stress, zones which are of no interest to the measurement or which disturb the measurement, are eliminated. This process therefore makes it possible, in cases where the calibration was not made in an identical configuration of the threaded rod and of the nut, to eliminate from the characteristic path of the acoustic ray the zones which are free from stress and/or are subjected to non-uniform stress, and which are a cause of error in the measurement of stress because the distribution of stresses is poorly defined there and because they influence the transit time by affecting the speed of the wave and the length of the characteristic run.

The process of the invention therefore no longer requires calibration for each position of the nut in the case of its application to a bolted structure. An equivalent remark may be made in the case of a threaded rod or of a tie threaded or anchored in a solid mass.

Even if the support surfaces of the bolt head and of the nut are not parallel because of flexion, the effect of flexion on the measurement is considerably reduced in comparison with known processes. In fact, the reflectors are smaller and the path of the waves is the path connecting by a straight line the two reflectors disposed on the slightly incurved neutral line. The error due to the difference between the length of the chord and the length of the arc formed by the neutral axis is not substantially modified, but the useful acoustic ray is propagated in a medium close to the axis of the part where the disturbing stress due to flexion can usually be considered as negligible, whereas in known processes this ray is displaced into the zone of compression introduced by the flexion. In the process of the invention a close approach is therefore made to measurement of stress along the axis of the part if the artificial reflectors are situated on that axis.

In view of the fact that use is made of the transit time of the useful acoustic ray on the path separating the two artificial reflectors, the disadvantages connected with the reflection peak on entry into the part and also the disadvantages connected with coupling, coupling pressure, surface state, wear and bruising of the ends of the bolt, etc., are eliminated.

It would also be possible to become independent of differences in the positioning of the sensor on the bolt head by utilizing the transit times statistically, for example by utilizing the mathematical expectation or an estimation thereof, of the transit times obtained for various positions and orientations of the sensor on the bolt head.

By utilizing small (quasi-punctiform or equivalent) artificial reflectors, the sensor will advantageously always be situated in the same place on the head, failing which no signal will be picked up or signals of different energies will be picked up.

This positioning is made possible by the presence of the artificial internal reflectors. It will, however, possibly necessitate the use of a conventional apparatus making it possible to display the amplitude of reflection echo peaks relating to the internal artificial reflectors in a type A representation or equivalent, in such a manner as to position the sensor at the point where the reflection echo peaks of the two artificial reflectors are, if possible, respectively identical in amplitude to the peaks obtained during the calibration.

As it is known that the acoustic energy transmitted depends, among other factors, on the thickness of the coupling liquid and the pressure applied to the sensor, it is at least necessary that the relative heights of the peaks should be substantially in the same ratio as during the calibration, which is equivalent to saying that the proportions of the energy transmitted into the bolt and reflected by each reflector to the receiver should be substantially identical.

For certain configurations of artificial reflectors, namely for example concentric axial bores of different diameters, as a rule the echo reflection peaks of the two artificial reflectors will as far as possible be simultaneously at their maximum when the axis of the beam substantially coincides with the axis of the bolt.

With regard to this problem of the positioning of the sensor on the end of the bolt, the following considerations may be set down:

The measurement of stress poses no problem when the sensor remains in a fixed position on the end of the bolt.

When for each measurement it is necessary to remove and replace the sensor, if the artificial reflectors are for example at a distance of about one meter from the sensor, no substantial random variations of transit time attributable to the positioning of the sensor will be observed. For certain types of reflector it does however occur that two or more families of characteristic transit times are shown.

In cases where the reflectors are bores orthogonal to the stem of the bolt and form a certain angle to one another, this is due to the reflection by the second reflector on each side of the shadow created by the first.

When the reflectors are brought close to the end where the sensor is situated, a random variation of the transit time relating to each family is observed, depending on the position of the sensor. These differences are due, among other factors, to a parallax effect, to the imperfect geometry of the reflectors, to faulty alignment of the cylindrical reflectors, to defects in the sensor, for example non-parallelism of the crystal to the contact face, and non-uniformity of the acoustic energy in the beam.

It may therefore be advantageous to have available a geometrical positioning of the sensor on the contact face, such as for example a positioning bush or a socket in the end of the part.

In addition, the presence of the internal reflectors no longer makes it necessary to generate and receive the acoustic wave by contact. It would be possible to generate the wave without contact with the bolt by taking advantage of magnetostriction in the case of ferromagnetic materials or of the mechanical shaking produced by the impact of a laser ray.

It is therefore found that the process of the invention is more accurate than known processes, and that it enables the disadvantages mentioned to be eliminated.

It should also be noted that the process of the invention is extremely simple and that the invention resides precisely in this extremely simple solution, whereas all previous attempts to find solutions seek to achieve a partial improvement of the processes or to eliminate only some disadvantages, for example by imposing strict requirements in respect of the quality of the end surfaces of bolts, etc., without ever eliminating all the disadvantages.

In the course of the description of the present invention reference is made in general, by way of illustration, to bolts. It should be noted that the invention provides a much awaited solution in this field of mechanical engineering. The application of the present invention is however not limited to bolts; it is possible to quote any connection means, such as threaded rods, studs, rivets, etc., or even any structural component or element.

The field of application is not limited to steel. Stress may be analysed or measured in any material, even in so-called plastic materials provided that they are permeable to acoustic waves at the useful frequencies.

According to one embodiment of the invention the artificial reflectors consist of transverse perforations or bores. These are advantageously disposed in parallel planes, forming an angle to one another. The two reflectors are preferably at right angles to one another. In the case of parts subjected to torsion it may be advantageous to dispose the perforations or bores at an angle between 0° and 90° and in a direction such that this angle increases with the angular torsional deformation.

According to another embodiment of the invention the reflectors consist of two coaxial bores of small diameter, but having different diameters and different depths, the difference in depth determining the utilized zone of transit of the useful acoustic ray. The transition zone between the two bores advantageously has a sharp edge and a plane connecting surface, perpendicular to the axis. It is advantageous for the acoustic ray to penetrate into the part via the end opposite the bore. It is certainly possible to find other possibilities for reflectors and the invention is not limited to the cases of application mentioned nor to the particular form of construction indicated for the reflectors.

The present invention also relates to parts characterized in that they are provided with artificial reflectors.

By "part" is understood in particular connection elements, for example high-strength bolts, threaded smooth or ribbed rods, rivets, studs, or else structural elements, particularly beams or other constructional elements.

These parts are advantageously provided with a means for the geometrical positioning of the sensor on the contact face, particularly a positioning bush or a socket in the end of the part.

With a view to better explaining the present invention, the latter will be described below with reference to the accompanying drawings, in which.

Figure 1A:
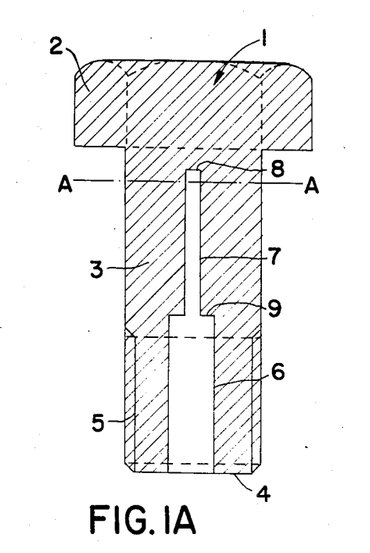
FIG. 1A shows a view in longitudinal section of a high-strength bolt provided with two artificial reflectors.
Figure 1B:
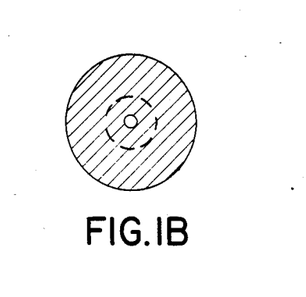
FIG. 1B is a section on the line A—A in FIG. 1A.

FIG. 1 shows by way of example a high-strength bolt 1 comprising a head 2 and a body 3 provided with a screwthread 5 at the end 4 opposite to the head. From the end 4 of the bolt 1 two coaxial bores 6, 7 of different diameters were machined. The bore 6 advantageously has a diameter larger than that of the bore 7 in order not to be masked by the "shadow" formed by the first reflector 8 consisting of the bottom of the bore 7 when the sensor disposed on the head 2 transmits an ultrasonic wave through the bolt. The second artificial reflector is formed by the shoulder 9. The bores are advantageously disposed on the axial line of the bolt.

It is therefore seen that it is possible to dispose the reflectors 8 and 9 in such a manner that the zone of measurement is disposed solely in the selected zone of stress. In the present case of application the part of the bolt body lying between the support surface of the head and the screwthread engaged in the nut is the zone in which the stress is considerable.

For the measurements use was made of an apparatus intended for ultrasonic thickness measurements, of the UTG 5A-IIB-SONATEST type, which automatically calculates the difference between the appearances of the feet of peaks of the two echoes resulting from the reflection of the useful acoustic ray on the two artificial reflectors, eliminating the other echoes, in particular the echo from the beginning and the bottom of parts and, where applicable, the parasitic echoes of the part beyond the second artificial reflector, for example those resulting from edges and inclined surfaces of the screwthreads.

Figure 2A:
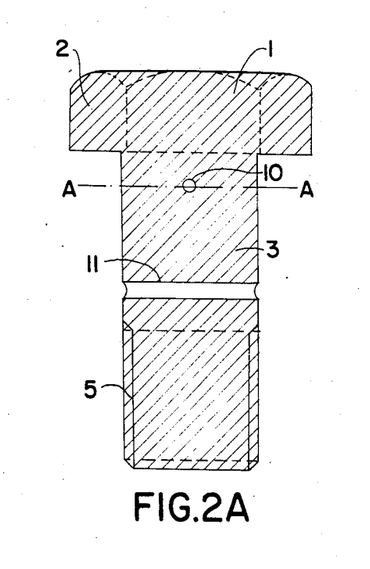
FIG. 2A shows a view in longitudinal section and another type of high-strength bolt provided with artificial reflectors.
Figure 2B:
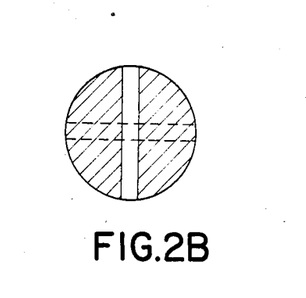
FIG. 2B is a section on the line A—A in FIG. 2A.

FIG. 2 shows another way of forming artificial reflectors. Two transverse holes have been made in the body 3 of the bolt 1, perpendicular to the axis of the latter. The holes 10,11 are advantageously situated in parallel planes, while forming an angle in relation to one another by projection onto one of the planes in such a manner as to intersect, for example, on the axial line. The two perforations 10,11 are advantageously perpendicular to one another.

It is also possible to imagine a bolt having a bore similar to the bore 7 in FIG. 1 and a transverse perforation similar to the perforation 11 in FIG. 2. The ultrasonic waves will thus be reflected by the bottom of the bore 7 and by the wall of the bore 11. In addition, the reflectors may be positioned so that the transit times of the disturbing echoes of the screwthreads will be longer than the transit time of the useful acoustic ray reflected on the most distant artificial reflector. In this way, they do not disturb the measurement in the first run of the wave.

It is also possible to imagine a truss system in a civil engineering structure, provided with transverse perforations similar to the perforations 10 and 11 in FIG. 2 and reproduced in each zone of the bar where knowledge of the stress is useful, these perforations being disposed in such a manner that they do not form acoustic screens in relation to one another, this being achieved, for example, by judicious selection of their respective angles.

It is clearly understood that in the application of the stress measuring process according to the invention it may, depending on circumstances, be desirable to take into account disturbing effects of factors other than stress, which may give rise to variations of the transit time of the useful acoustic ray, such as, for example, the temperature, and to make the necessary correction.

The measurement of the temperature could be made simultaneously with the measurement of the stress by suitably incorporating in the sensor a temperature detector, such as for example a thermocouple.

Figure 3:
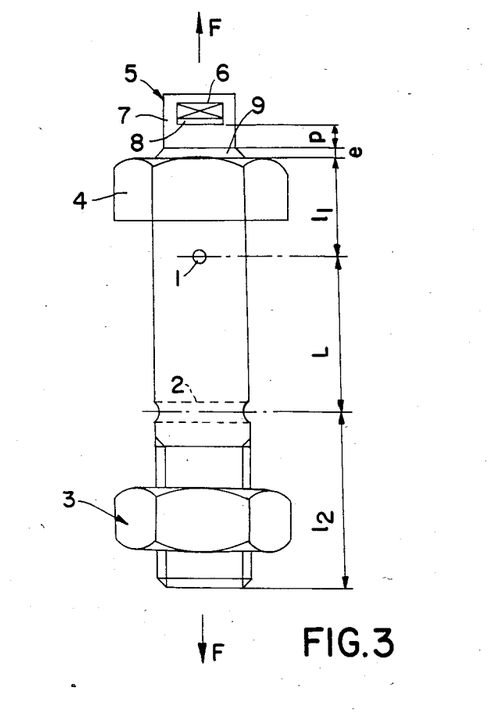
FIG. 3 illustrates an application of the measuring process according to the invention to the measurement of stress in a bolt.

FIG. 3 shows a bolt provided with two artificial internal reflectors, consisting in this particular case of transverse bores 1 and 2 disposed diametrically in two parallel planes perpendicular to the axis of the bolt. The bolt is provided with a nut 3. On the head 4 of the bolt has been disposed an ultrasonic transmitter/receiver sensor 5 containing a piezoelectric crystal 8, a plexiglass delay line 7, and absorbent material 6. Between the sensor 5 and the end of the bolt 10 there is a coupling liquid 9.

The length of the path amounts to p in the plexiglass, to e in the coupling liquid, to $l_1$ in the bolt as far as the first reflector, to L between the two reflectors, and to $l_2$ between the second reflector and the end.

The bolt is subjected to a force F which brings about a variation of the characteristic transit time of the useful acoustic ray between the two reflectors.

Figure 4:
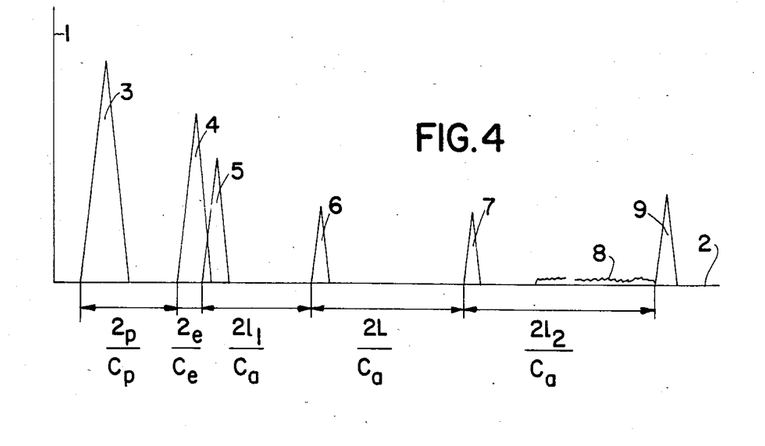
FIG. 4 illustrates the type A representation obtained in the case of the application shown in FIG. 3.

FIG. 4 shows type A representation of the results obtained. On the ordinate 1 is shown the height of the transmission or reflection peaks and on the abscissa 2 the transit time.

The peak 3 is connected to the excitation of the crystal 8 in FIG. 3.

The peak 4 is related to the reflection at the interface between the plexiglass and the coupling liquid.

The peak 5 is related to the reflection at the interface between the coupling liquid and the steel.

The peak 6 is related to the reflection on the reflector 1 in FIG. 3.

The peak 7 is related to the reflection on the reflector 2 in FIG. 3.

The peaks 8 are related to the reflections on the faces and edges of the screwthread.

The peak 9 is related to the reflection on the end of the bolt.

On the abscissa, the values of the different characteristic times are indicated.

$C_p$ is the speed of the ultrasonic wave in the plexiglass.

$C_e$ is the speed of the ultrasonic wave in the oil.

$C_a$ is the speed of the ultrasonic order in the steel.

Figure 5:
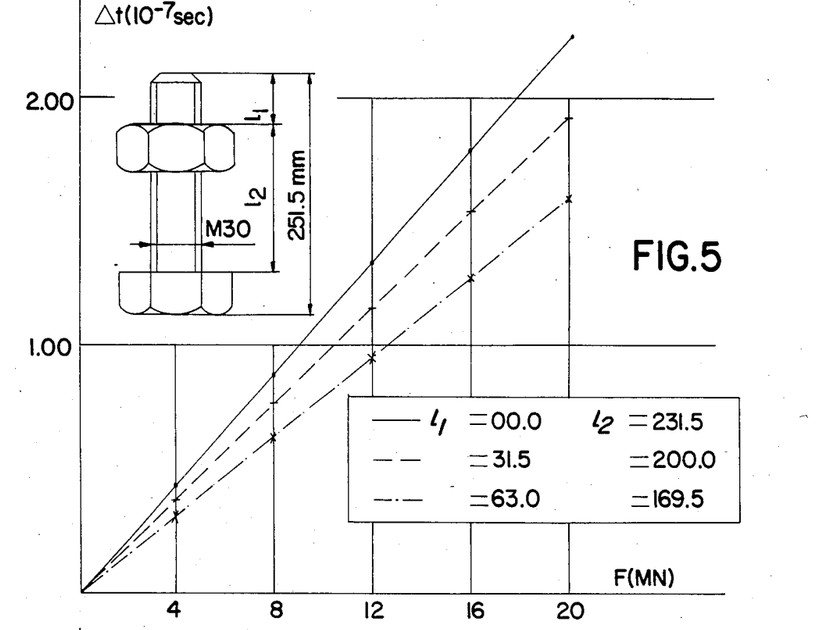
FIG. 5 is the graphical representation of the variations of the transit time of the useful acoustic ray in the case of a threaded M30 rod of steel plotted against the stress for different respective configurations of the connection element constituted by the threaded rod and its two nuts when the measurement of stress is made in accordance with the known process.
Figure 6:
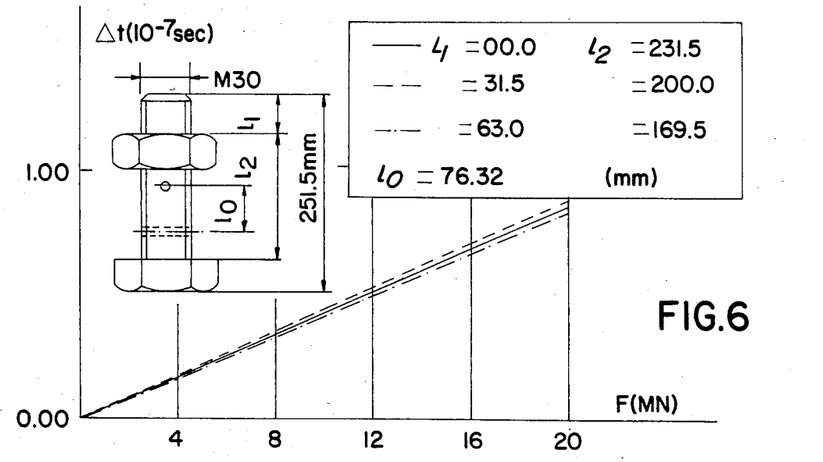
FIG. 6 is the graphical representation of the variations of the transit time of the useful acoustic ray in the case of a threaded M30 rod of steel plotted against the stress for different respective configurations of the connection element constituted by the threaded rod and its two nuts when the measurement of stress is made in accordance with the process of the invention on a threaded rod in which artificial reflectors have been formed, which consist of transverse perforations disposed in parallel planes at a distance $l_o$ apart and forming an angle of 90° with one another.

In FIGS. 5 and 6 the variation of the transit time between the two ends of the threaded M30 rod is shown on the ordinate. On the abscissa is shown the tensile load in the tensioned portion of the threaded M30 rod between the two nuts with a length $l_2$ equal to to 231.5, 200 and 169.5 mm.

A straight line corresponds to each configuration of the connection element.

In the case of application shown in FIG. 5, the straight lines are appreciably different, whereas in the case of application shown in FIG. 6 the straight lines substantially coincide; the differences in this case originate no doubt from the slightly different positioning of the sensor for each configuration of the connection.

I claim:

1. Process for the measurement of stress in a structural element by making use of the reflection of an acoustic wave and by measuring a transit time of the latter with the aid of an equipment measuring the time of appearance of an echo coming from an interface, wherein one or a plurality of ends of rectilinear measurement paths, having the material form of an internal artificial reflector, is or are selected in the medium, wherein a beam of acoustic waves is transmitted in such a manner that acoustic rays carrying sufficient energy touch the useful reflectors, wherein the echoes corresponding to the reflectors are selected, wherein the transit times characteristic of the useful acoustic rays as far as the internal artificial reflectors are determined by measurement, and wherein the transit times for each internal reflector considered individually, or the respective differences of transit time of each pair of reflectors, are transposed into a value of external stress or into a value of stress in the zone delimited by each pair of reflectors.

2. Process as claimed in claim 1, wherein a rectilinear measurement path bounded by two internal artificial reflectors is selected in the medium, wherein a beam of acoustic waves, the axis of which is substantially identical with the selected rectilinear measurement path, is transmitted, wherein the echoes corresponding to the internal artificial reflectors are selected, wherein the transit time characteristic of an acoustic ray between the two reflectors is measured, this time being the difference between the transit times of the coincident or substantially parallel acoustic rays as far as each of the two reflectors, and wherein the values of transit time are transposed into values of stress.

3. Process as claimed in claim 1, wherein a narrow ultrasonic beam is used.

4. Process as claimed in claim 1, wherein a focused ultrasonic beam is used.

5. Process as claimed in claim 1, wherein the measurement is made by continuous transmission and determination of the resonance frequencies of the wave which are due to the two internal reflectors.

6. Process as claimed in claim 1, wherein transverse ultrasonic waves are used.

7. Process as claimed in claim 1, wherein longitudinal ultrasonic waves are used.

8. Process as claimed in claim 1, wherein surface ultrasonic waves are used.

9. Process as claimed in claim 1, wherein a longitudinal wave and a transverse wave are used in combination, concomitantly or in succession.

10. Process as claimed in claim 1, wherein the artificial reflectors consist of transverse perforations or bores disposed in parallel planes and forming an angle in relation to one another.

11. Process as claimed in claim 1, wherein the reflectors consist of two coaxial bores of small diameter, but of different diameters and of different depths.

12. Process as claimed in claim 1, wherein the positioning of the transmitter/receiver sensor is effected by finding the position in which the amplitudes of the reflection echoes on the internal artificial reflectors are as far as possible simultaneously maximum or attain respective relative heights marked in advance during the calibration.

13. Process as claimed in claim 1, wherein the measurement is made by utilizing two different frequencies of acoustic waves.

14. Structural element for performing the process as claimed in claim 1, which has one or more artificial reflectors (8, 9) for the acoustic waves.

15. Structural element as claimed in claim 14, which consists of a bolt, a threaded rod, or a tie.

16. Structural element as claimed in claim 14, which is provided with artificial reflectors (8, 9) which consist of transverse perforations or bores disposed in parallel planes and forming an angle in relation to one another.

17. Structural element as claimed in claim 16, in which the perforations or bores (10, 11) form an angle of 90° between them.

18. Structural element as claimed in claim 16, in which the perforations or bores (10, 11) form an angle between 0° and 90° in such a direction that this angle increases with the angular torsional deformation on tightening.

19. Structural element as claimed in claim 14, which is provided with positioning means such as a bush or a socket in the end of the part intended to receive a sensor.

20. Process for the measurement of stress in a structural element by making use of the reflection of an acoustic wave and by measuring a transit time of the latter with the aid of an equipment measuring the time of appearance of an echo coming from an interface, wherein one or a plurality of ends of rectilinear measurement paths, having the material form of an internal artificial reflector, is or are selected in the medium, wherein a beam of acoustic waves is transmitted in such a manner that acoustic rays carrying sufficient energy touch the useful reflectors, wherein the echoes corresponding to the reflectors are selected, wherein the transit times characteristic of the useful acoustic rays as far as the internal artificial reflectors are determined by measurement, and wherein the transit times for each internal reflector considered individually, or the respective differences of transit time of each pair of reflectors, are transposed into a value of external stress or into a value of stress in the zone delimited by each pair of reflectors; and     wherein the artificial reflectors consist of transverse perforations or bores disposed in parallel planes and forming an angle in relation to one another, said perforations or bores forming an angle of 90° between them.

21. Process for the measurement of stress in a structural element by making use of the reflection of an acoustic wave and by measuring a transit time of the latter with the aid of an equipment measuring the time of appearance of an echo coming from an interface, wherein one or a plurality of ends of rectilinear measurement paths, having the material form of an internal artificial reflector, is or are selected in the medium, wherein a beam of acoustic waves is transmitted in such a manner that acoustic rays carrying sufficient energy touch the useful reflectors, wherein the echoes corresponding to the reflectors are selected, wherein the transit times characteristic of the useful acoustic rays as far as the internal artificial reflectors are determined by measurement, and wherein the transit times for each internal reflector considered individually, or the respective differences of transit time of each pair of reflectors, are transposed into a value of external stress or into a value of stress in the zone delimited by each pair of reflectors; and     wherein the artificial reflectors consist of transverse perforations or bores disposed in parallel planes and forming an angle in relation to one another, said perforations or bores forming an angle between 0° and 90° in a direction such that this angle increases with the angular torsional deformation on tightening.

* * * * *